United States Patent [19]

Lewis et al.

[11] 4,119,781

[45] Oct. 10, 1978

[54] PROCESS FOR PREPARING 4-SUBSTITUTED IMIDAZOLE COMPOUNDS

[75] Inventors: Joseph J. Lewis; Robert L. Webb, both of West Chester, Pa.

[73] Assignee: SK&F Lab Co., Carolina, P.R.

[21] Appl. No.: 771,044

[22] Filed: Feb. 22, 1977

Related U.S. Application Data

[63] Continuation-in-part of Ser. No. 626,948, Oct. 29, 1975, abandoned.

[51] Int. Cl.$^2$ .................. C07D 233/64; C07D 233/84
[52] U.S. Cl. .............................. 548/337; 260/293.7; 544/139; 548/315; 548/336; 548/342
[58] Field of Search ................ 548/342, 336, 315, 337

[56] References Cited

U.S. PATENT DOCUMENTS 3,325,546   6/1967   Hays .............................. 260/606.5 P

OTHER PUBLICATIONS

Houben-Weyl, Methoden der Organischen Chemie, vol. XXI, part I, p. 51 (1963).
Zbiral et al., Phosphorus 1972, vol. 2, pp. 29-34.
Berlin et al., Chem. Review 1960, vol. 60, pp. 247-248.
Zbiral, Synthesis 1974, vol. 11, pp. 775-797.
Aksnes et al., Chem. Abst. 1962, vol. 57, cols. 14473-14474.
Allen et al., Chem. Abst. 1974, vol. 80, No. 47138t.
Grayson et al., J. Amer. Chem. Soc. 1959, vol. 81, pp. 4803-4807.
House Modern Synthetic Reactions, pp. 701-702, W. A. Benjamin, 1972.
Organic Reactions, vol. 14, pp. 278-279, N.Y., Wiley, 1965.
Zbiral et al., Tetrahedron Letters 1972, No. 5, pp. 439-444.

*Primary Examiner*—Natalie Trousof
*Attorney, Agent, or Firm*—Joan S. Keps; Richard D. Foggio; William H. Edgerton

[57] ABSTRACT

A process for preparing 4-(oxy, thio or amino)methylimidazole compounds via displacement of the trisubstituted phosphonium group from 4-(trisubstituted phosphonium)methylimidazole compounds is disclosed.

14 Claims, No Drawings

PROCESS FOR PREPARING 4-SUBSTITUTED IMIDAZOLE COMPOUNDS

This application is a continuation-in-part of Ser. No. 626,948 filed Oct. 29, 1975, now abandoned.

This invention relates to a process for preparing substituted imidazole compounds which are useful intermediates in the preparation of compounds having pharmacological activity. In particular, the invention relates to a process for preparing 4-(oxy, thio or amino)-methylimidazoles via displacement of the trisubstituted phosphonium group from a 4-(trisubstituted phosphonium)-methylimidazole compound which is represented as follows:

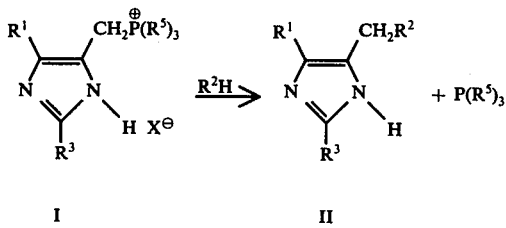

I  II in which $R^1$ is hydrogen or lower alkyl, preferably methyl; $R^2$ is methoxy, ethoxy, n-propoxy, n-butoxy, i-butoxy, t-butoxy, $-SCH_2CH_2NH_2$,

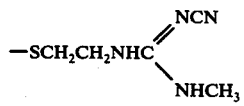

or $-NR^6R^7$ where $R^6$ and $R^7$ are each hydrogen, lower alkyl or together with the nitrogen atom to which they are attached form a piperidine, pyrrolidine or morpholine ring; $R^3$ is hydrogen, lower alkyl, trifluoromethyl, benzyl, amino or $-SR^4$ where $R^4$ is lower alkyl, preferably methyl, phenyl, benzyl or chlorobenzyl; $R^5$ is lower alkyl or, preferably, phenyl and X is halo, preferably chloro or bromo. Preferably, $R^2$ is $-SCH_2CH_2NH_2$ or

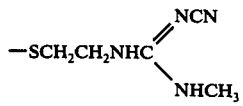

Particular processes of this invention comprise the process represented above wherein $R^5$ is phenyl and (1) $R^2$ is $-SCH_2CH_2NH_2$ and $R^3$ is $-SR^4$ where $R^4$ is methyl, (2) $R^2$ is $-SCH_2CH_2NH_2$ and $R^3$ is hydrogen or (3) $R^2$ is

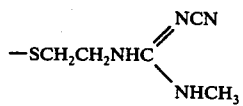

and $R^3$ is hydrogen.

The 4-(trisubstituted phosphonium)methylimidazole compounds of Formula I are also objects of this invention.

As used herein, the term "lower alkyl" refers to groups containing from one to four carbon atoms.

According to the above process, the displacement of a trisubstituted phosphonium group $[-P^\oplus(R^5)_3]$ of a compound of formula I is effected by reaction of a compound of formula I with $R^2H$ under basic conditions, that is with $R^2H$ in the form of its anion $R^{2\ominus}$. The anion may be formed from in situ reaction of a compound of the formula $R^2H$ and a strong base. Among the bases which may be used in the process of this invention are those which are capable of removing the proton from a compound of the formula $R^2H$ to form the anion $R^{2\ominus}$ where $R^2$ is defined as above. Such bases are those having a pKa greater than 12, for example the alkali metal alkoxides such as sodium methoxide or ethoxide or the metal hydrides such as sodium hydride which are preferred. When $R^2H$ is itself sufficiently basic, for example when $R^2H$ is piperidine, no additional base need be used. In those cases where $R^2H$ is extremely volatile, such as when $R^2$ is $-NR^6R^7$ and one or both of $R^6$ and $R^7$ are hydrogen, it is preferable that $R^2H$ be in the form of a metalate, for example sodium or lithium metalate, such as sodium amide. Preferably, a slight excess of $R^2H$ is present.

The reaction is carried out in an organic solvent with solvents such as methanol, ethanol, propanol, butanol, acetone, acetonitrile, dimethylformamide and dimethylsulfoxide being preferred. Preferably, the reaction is carried out at a temperature ranging from about ambient temperature to the reflux temperature of the solvent used in the reaction, viz. from about 25° C. to about 200° C., about 65° C. to about 100° C. being advantageous, for from about 20 minutes to about 24 hours, advantageously from about 20 minutes to about 3 hours.

Preferably, the reaction mixture is worked up by dilution with water and removal of the trialkyl- or triphenylphosphine by-product by filtration. Extraction of the filtrate when necessary followed by evaporation gives the compounds of formula II. It is often desirable to convert the compounds of formula II to the corresponding salts, preferably hydrochloride salts. Such salts are prepared by treating a solution of the imidazole of formula II with an acid or acid solution, for example with an ethereal or ethanolic solution of hydrochloric acid, and crystallizing the salt produced from an appropriate solvent.

The 4-(trisubstituted phosphonium)-methylimidazoles of formula I are prepared from reaction of a trisubstituted β-acylvinylphosphonium halide, preferably bromide or chloride, of the formula

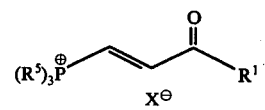

where $R^1$, $R^5$ and X are defined as above with a compound of the formula

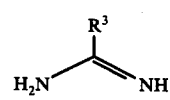

where $R^3$ is defined as above other than hydrogen, according to the procedure described by Zbiral, Synthesis 11:775 (1974) and Zbiral and Hugl, *Phosphorus* 2:29 (1972). When $R^3$ is hydrogen, the corresponding 4-(trisubstituted phosphonium)methylimidazoles of formula I are also prepared by reaction of trichloroacetamidine or formamidine sulfinic acid with a triphenyl β-acylvinylphosphonium halide. In the formamidine sulfinic acid process a base is used, preferably a non-nucleophilic base such as a tertiary amine.

To prepare the trisubstituted β-acylvinylphosphonium halides not known to the art, a halovinyl alkyl ketone such as chlorovinyl methyl ketone is treated with a trialkyl- or triphenylphosphine. When $R^1$ is hydrogen, the trisubstituted β-formylvinylphosphonium halides are prepared by oxidation of a β-haloallyl alcohol such as β-chloroallyl alcohol and treatment of the product thus formed with a trialkyl- or triphenylphosphine.

The process of this invention provides an inexpensive, efficient and high yield method for preparing certain imidazoles useful as intermediates in the preparation of pharmacologically active compounds. A further advantage of this process for the conversion of compounds of formula I to those of formula II is that the trisubstituted phosphines, $P(R^5)_3$, formed during the course of the reaction may be easily removed from the reaction mixture and recycled or otherwise reused.

The imidazole compounds of formula II prepared by the process of this invention are useful as intermediates for the production of pharmacologically active compounds in particular histamine $H_2$-antagonists, for example N-cyano-N'-methyl-N''-[2-(5-$R^1$-imidazolylmethylthio)ethyl]-guanidine and N-methyl-N'-[2-(5-$R^1$-imidazolylmethylthio)-ethyl]thiourea compounds. Histamine $H_2$-antagonists act at histamine $H_2$-receptors which as described by Black et al. [*Nature* 236:385 (1972)] may be defined as those histamine receptors which are not blocked by "antihistamines" such as mepyramine but are blocked by burimamide. Blockade of histamine $H_2$-receptors is of utility in inhibiting the biological actions of histamine which are not inhibited by "antihistamines". Histamine $H_2$-antagonists are useful, for example, as inhibitors of gastric acid secretion.

Conversion of the compounds of formula II to the pharmacologically active guanidine and thiourea products can be accomplished in a variety of ways. When $R^2$ is —$SCH_2CH_2NH_2$ and $R^3$ is hydrogen, lower alkyl, trifluoromethyl, benzyl or amino, the 4-(2-aminoethyl)-thiomethylimidazole compound of formula II is treated with methyl isothiocyanate to give the corresponding N-methyl-N'-[2-(5-$R^1$-imidazolylmethylthio)ethyl]thioureas. Reaction of the same 4-(2-aminoethyl)thiomethylimidazole compound with N-cyano-N',S-dimethylisothiourea gives the corresponding N-cyano-N'-methyl-N''-[2-(5-$R^1$-imidazolylmethylthio)-ethyl]guanidines. The guanidine products are also prepared by reaction of the 4-(2-aminoethyl)-thiomethylimidazole with dimethyl-N-cyanoimidodithiocarbonate and subsequently reacting the resulting N-cyano-N'-[2-(5-$R^1$-imidazolylmethylthio)ethyl]-S-methylisothiourea with methylamine. When $R^2$ is

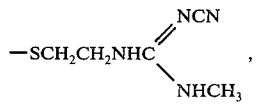

the guanidine products are prepared directly by the process of this invention.

When $R^2$ is —$SCH_2CH_2NH_2$ and $R^3$ is —$SR^4$ where $R^4$ is defined as above, the compounds of formula II are treated with a reducing agent, for example, with Raney nickel, to give the corresponding 4-(2-aminoethyl)thiomethylimidazoles where $R^3$ is hydrogen which are then converted to the guanidine and thiourea products as described above. When $R^2$ is

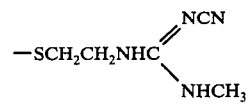

and $R^3$ is —$SR^4$, treatment with a reducing agent gives the guanidine product directly.

When $R^2$ is methoxy, ethoxy, n-propoxy, n-butoxy, i-butoxy, t-butoxy or —$NR^6R^7$ and $R^3$ is —$SR^4$ where $R^4$ is defined as above, the —$SR^4$ group of the compounds of formula II is removed as described above and the products thus formed are then treated with cysteamine to give the 4-(2-aminoethyl)thiomethylimidazole compounds where $R^3$ is hydrogen which are converted to the guanidine and thiourea products as previously described.

When $R^2$ is methoxy, ethoxy, n-propoxy, n-butoxy, i-butoxy, t-butoxy or —$NR^6R^7$ and $R^3$ is hydrogen, the compounds of formula II are treated with cysteamine to give the 4-(2-aminoethyl)thiomethylimidazoles which are then converted to the guanidine and thiourea products as previously described.

These thiourea and cyanoguanidine products prepared from the compounds of formula II are described in U.S. Pat. Nos. 3,950,333 and 3,950,353.

The following examples illustrate the invention but are not intended to limit the scope thereof. Temperatures are in degrees Centigrade (° C.) unless otherwise indicated.

EXAMPLE 1

Sodium metal (25.3 g., 1.1 mole) was dissolved in ethanol (2 L). 2-Methylpseudothiourea sulfate (278.3 g., 1.0 mole) was added and the mixture was stirred for 0.5 hour. Then 411 g. (1.0 mole) of triphenyl β-acetylvinylphosphonium bromide was added and the mixture was heated at reflux for 18 hours, cooled and filtered. The filter cake was washed with 200 ml. of ethanol. The filtrate and ethanol wash were combined and evaporated under reduced pressure to leave a brown residue. Chloroform (500 ml.) was added to the residue and the mixture was stirred for a few minutes, then filtered. The filter cake was washed three times with 150 ml. portions of chloroform and dried to give 364 g. (75%) of [(2-methylthio-5-methylimidazolyl)-4-methyl]triphenylphosphonium bromide.

Cysteamine (12.23 g., 0.13 mole) was dissolved in 100 ml. methanol and 46.5 ml. of 25% wt/v sodium methoxide solution added. After stirring at ambient temperature for 10 minutes, the solid phosphonium salt was added and the mixture was refluxed for 20 minutes. The solution was diluted with twice its volume of ice water and stirred. The precipitated triphenyl phosphine was removed by filtration. The filtrate was extracted with three 100 ml. portions of chloroform and the chloroform extracts were dried and evaporated to dryness to yield 19 g. (86%) of 4-(2-aminoethyl)thiomethyl-5-methyl-2-methylthioimidazole as a viscous oil.

Treatment of 4-(2-aminoethyl)thiomethyl-5-methyl-2-methylthioimidazole with ethanolic hydrochloric acid gave the corresponding dihydrochloride salt, m.p. 165° (ethanolethyl acetate).

EXAMPLE 2

A solution of 48.3 g. (0.1 mole) of [(5-methyl-2-methylthioimidazolyl)-4-methyl]triphenylphosphonium bromide in 250 ml. of methanol was added rapidly at ambient temperature to a stirred solution of 35 ml. of 25% sodium methoxide in methanol in 250 ml. of methanol. The mixture was refluxed for 20 minutes then concentrated to half the volume. After dilution with 900 ml. of water, the triphenyl phosphine was removed by filtration. The aqueous solution was extracted twice with 150 ml. portions of benzene and then three times with 250 ml. portions of chloroform. The chloroform extracts were dried (MgSO$_4$) and evaporated to dryness to give 13 g. (76%) of 4-methoxymethyl-5-methyl-2-methylthioimidazole.

EXAMPLE 3

Sodium metal (2.3 g., 0.1 mole) was dissolved in ethanol and 9.5 g. (0.1 mole) of acetamidine hydrochloride was added with stirring. After 10 minutes 41.1 g. (0.1 mole) of triphenyl β-acetylvinylphosphonium bromide was added and the mixture was refluxed for 17 hours. The mixture was filtered and the filtrate evaporated to dryness to give a tan solid which was digested with 300 ml. of chloroform. Ethyl acetate (100 ml.) was added and the precipitate was collected by filtration and washed with 100 ml. of acetone to give 36 g. (80%) of [(2,5-dimethylimidazolyl)-4-methyl]triphenylphosphonium bromide.

When an equivalent amount of [(2,5-dimethylimidazolyl)-4-methyl]triphenylphosphonium bromide is substituted into the procedures of Examples 1 and 2 for [(2-methylthio-5-methylimidazolyl)-4-methyl]triphenylphosphonium bromide, 4-(2-aminoethyl)thiomethyl-2,5-dimethylimidazole and 2,5-dimethyl-4-methoxymethylimidazole are prepared, respectively.

EXAMPLE 4

(a) Trichloroacetamidine (1.62 g., 0.1 mole) was dissolved in 20 ml. of dry dimethylsulfoxide and 4.1 g. (0.1 mole) of triphenyl β-acetylvinylphosphonium bromide in 40 ml. of dimethylsulfoxide was added in one portion with stirring. The exothermic reaction mixture gradually lightened in color and was heated at 100° for 10 minutes. Evaporation of the solvent gave [(5-methylimidazolyl)-4-methyl]triphenylphosphonium bromide.

Alternatively, and preferably, the phosphonium bromide is prepared using trichloroacetamidine by the following procedures:

Triphenyl β-acetylvinylphosphonium bromide (8.0 g., 0.019 mole) was dissolved in a minimum amount of dry acetonitrile (about 100 ml.) and trichloroacetamidine (4.0 g., 0.25 mole) was added in one portion. The resulting mixture was stirred at room temperature and the material which crystallized out was filtered off to give [(2-trichloromethyl-5-methylimidazolyl)-4-methyl]triphenylphosphonium bromide.

This phosphonium salt (15.0 g., 0.027 mole) was added to 150 ml. of methanol and the resulting mixture was refluxed for 3 hours. The mixture was concentrated to about 15 ml. and the solid material was filtered off to give [(2-methoxycarbonyl-5-methylimidazolyl)-4-methyl]triphenylphosphonium bromide.

The above prepared phosphonium salt is heated to its melting point (approximately 170°) and held at this temperature until the evolution of gas is complete. On cooling, the solid product is triturated with chloroform to give [(5-methylimidazolyl)-4-methyl]triphenylphosphonium bromide.

Triphenyl β-acetylvinylphosphonium chloride (36 g., 0.01 mole) and trichloroacetamidine (16.1 g., 0.1 mole) were stirred in 200 ml. of methanol for 1 hour. The solution was heated to reflux, cooled and the methanol evaporated to leave [(2-methoxycarbonyl-5-methylimidazolyl)-4-methyl]-triphenylphosphonium chloride. Heating this phosphonium chloride salt at 170° until evolution of gas is complete, then cooling and triturating with chloroform gives [(5-methylimidazolyl)-4-methyl]triphenylphosphonium chloride.

(b) Formamidine sulfinic acid (11.0 g., 0.1 mole) was suspended in 250 ml. of dry dimethylsulfoxide and 2.4 g. (0.1 mole) of sodium hydride was added. After cessation of hydrogen gas evolution 36.5 g. (0.1 mole) of triphenyl β-acetylvinylphosphonium chloride was added and the mixture was stirred for one hour at ambient temperature, then heated at 100° for 10 minutes. After cooling, the dimethylsulfoxide was evaporated and the residue was dissolved in 300 ml. of 1:1 chloroform-methanol and the solution filtered. The filtrate was evaporated to dryness and the residue was recrystallized from chloroformacetone to give 20 g. (50%) of [(5-methylimidazolyl)-4-methyl]triphenylphosphonium chloride, m.p. 223°–225°.

Alternatively, and preferably, [(5-methylimidazolyl)-4-methyl]triphenylphosphonium chloride and bromide are prepared using formamidine sulfinic acid by the following procedures:

Triphenyl β-acetylvinylphosphonium chloride (3.65 g., 0.01 mole) and formamidine sulfinic acid (1.1 g., 0.01 mole) were dissolved in 50 ml. of dimethylsulfoxide. 1,8-bis-(Dimethylamino)naphthalene ("proton sponge") (2.14 g., 0.01 mole) was added and the mixture warmed to 80°. After cooling, evaporating the dimethylsulfoxide, precipitating the inorganic salts with chloroform, filtering, evaporating to dryness and recrystallizing the residue from chloroformacetone, an essentially quantitative yield of [(5-methylimidazolyl)-4-methyl]triphenylphosphonium chloride was obtained.

Triphenyl β-acetylvinylphosphonium bromide (20.6 g., 0.05 mole) and formamidine sulfinic acid (6.0 g., slight excess over 0.05 mole) were dissolved in 100 ml. of dimethylsulfoxide. 1,5-Diazabicyclo[5.4.0]undec-5-ene (DBU) (7.6 g., 0.05 mole) was added dropwise with stirring. The mixture was maintained at 80° for 20 minutes and the dimethylsulfoxide was evaporated off. The residue was taken up in chloroform and inorganic salts were removed by filtration. The filtrate was evaporated to dryness and the residue was recrystallized from chloroformacetone to give [(5-methylimidazolyl)-4-methyl]triphenylphosphonium bromide in 80% yield.

To a solution of 39.3 g. (0.1 mole) of [(5-methylimidazolyl)-4-methyl]triphenylphosphonium chloride in 200 ml. of methanol was added 22 ml. of 25% sodium methoxide in methanol and the reaction mixture was refluxed for 1 hour. After cooling, the solution was diluted with 3 times its volume of water and filtered to remove triphenyl phosphine. The filtrate was extracted with four 125 ml. portions of chloroform and the extracts were dried (MgSO$_4$) and evaporated to dryness to yield 10.1 g. (80%) of 4-methoxymethyl-5-methylimidazole which was converted to the corresponding hydrochloride salt as described in Example 1, m.p. 150°.

EXAMPLE 5

Triphenyl β-acetylvinylphosphonium bromide (4.11 g., 0.01 mole) was added in one portion to a stirred suspension of 1.1 g. (0.01 mole) of formamidine sulfinic acid in 20 ml. of dimethylsulfoxide containing 0.25 g. of sodium hydride. The mixture was stirred at ambient temperature for 1 hour then at 80° for an additional hour. A solution of 0.99 g. (0.01 mole) of the sodium salt of cysteamine, prepared by addition of two equivalents of sodium methoxide to cysteamine dihydrochloride, in 10 ml. of methanol was added and the resulting mixture was heated at 70°-80° for 4 hours. The mixture was diluted with twice its volume of water and the triphenyl phosphine was removed by filtration. The filtrate was extracted with 100 ml. of toluene and with two 100 ml. portions of chloroform. The chloroform extracts were combined, dried (MgSO$_4$) and evaporated to dryness to give 4-(2-aminoethyl)thiomethyl-5-methylimidazole.

Alternatively, and preferably, the above described reaction of triphenyl β-acetylvinylphosphonium bromide and formamidine sulfinic acid is carried out using 1,8-bis-(dimethylamino)naphthalene or 1,5-diazabicyclo[5.4.0]undec-5-ene by the procedures described in Example 4(b).

EXAMPLE 6

When an equivalent amount of triphenyl β-ethylcarbonylvinylphosphonium bromide or triphenyl β-isopropylcarbonylvinylphosphonium bromide is allowed to react with formamidine sulfinic acid as described in the procedure of Example 4, [(5-ethylimidazolyl)-4-methyl]-triphenylphosphonium bromide and [(5-isopropylimidazolyl)-4-methyl]triphenylphosphonium bromide are prepared, respectively.

Reaction of [(5-ethylimidazolyl)-4-methyl]-triphenylphosphonium bromide and [(5-isopropylimidazolyl)-4-methyl]triphenylphosphonium bromide with cysteamine in the presence of sodium methoxide or sodium hydride as described above gives 4-(2-aminoethyl)thiomethyl-5-ethylimidazole and 4-(2-aminoethyl)thiomethyl-5-isopropylimidazole, respectively.

In a similar manner, the triphenylphosphonium group of [(5-ethylimidazolyl)-4-methyl]triphenylphosphonium bromide and [(5-isopropylimidazolyl)-4-methyl]triphenylphosphonium bromide is displaced by reaction with other nucleophiles by procedures described herein.

EXAMPLE 7

When [(5-methylimidazolyl-4-methyl]triphenylphosphonium bromide is allowed to react with sodium ethoxide in ethanol, sodium n-propoxide in n-propanol or sodium t-butoxide in t-butanol according to the procedure described in Example 4(b), the following imidazole compounds are obtained:
 4-ethoxymethyl-5-methylimidazole
 5-methyl-4-n-propoxymethylimidazole
 4-t-butoxymethyl-5-methylimidazole.

EXAMPLE 8

Substitution of a salt of a 2-substituted pseudothiourea listed below:
 2-ethylpseudothiourea
 2-butylpseudothiourea
 2-benzylpseudothiourea
 2-phenylpseudothiourea
 2-(4-chlorobenzyl)pseudothiourea
in the procedure of Example 1 in place of 2-methylpseudothiourea sulfate gives the following triphenylphosphonium bromide compounds:
 [(2-ethylthio-5-methylimidazolyl)-4-methyl]-triphenylphosphonium bromide
 [(2-butylthio-5-methylimidazolyl)-4-methyl]-triphenylphosphonium bromide
 [(2-benzylthio-5-methylimidazolyl)-4-methyl]-triphenylphosphonium bromide
 [(5-methyl-2-phenylthioimidazolyl)-4-methyl]-triphenylphosphonium bromide
 [(2-(4-chlorobenzyl)thio-5-methylimidazolyl)-4-methyl]triphenylphosphonium bromide.

Reaction of a triphenylphosphonium bromide listed above with cysteamine as described in Example 1 gives the imidazole compounds listed below:
 4-(2-aminoethyl)thiomethyl-2-ethylthio-5-methylimidazole
 4-(2-aminoethyl)thiomethyl-2-butylthio-5-methylimidazole
 4-(2-aminoethyl)thiomethyl-2-benzylthio-5-methylimidazole
 4-(2-aminoethyl)thiomethyl-5-methyl-2-phenylthioimidazole
 4-(2-aminoethyl)thiomethyl-2-(4-chlorobenzyl)-thio-5-methylimidazole.

EXAMPLE 9

Substitution of a salt of a substituted amidine listed below:
 guanidine
 propionamidine
 valeramidine
 2,2,2-trifluoroacetamidine
 2-phenylacetamidine
in the procedure of Example 3 for acetamidine hydrochloride gives the triphenylphosphonium bromides listed below:
 [(2-amino-5-methylimidazolyl)-4-methyl]triphenylphosphonium bromide
 [(2-ethyl-5-methylimidazolyl)-4-methyl]triphenylphosphonium bromide
 [(2-butyl-5-methylimidazolyl)-4-methyl]triphenylphosphonium bromide
 [(5-methyl-2-trifluoromethylimidazolyl)-4-methyl]-triphenylphosphonium bromide
 [(2-benzyl-5-methylimidazolyl)-4-methyl]triphenylphosphonium bromide.

Reaction of a triphenylphosphonium bromide listed above with cysteamine as described in the procedure of Example 1 gives the following imidazole compounds:
 2-amino-4-(2-aminoethyl)thiomethyl-5-methylimidazole
 4-(2-aminoethyl)thiomethyl-2-ethyl-5-methylimidazole
 4-(2-aminoethyl)thiomethyl-2-butyl-5-methylimidazole
 4-(2-aminoethyl)thiomethyl-5-methyl-2-trifluoromethylimidazole
 4-(2-aminoethyl)thiomethyl-2-benzyl-5-methylimidazole.

EXAMPLE 10

To a solution of 9.25 g. (0.1 mole) of β-chloroallyl alcohol in 100 ml. of benzene is added an equivalent amount of an aqueous solution of chromic acidsulfuric acid (Jones reagent) and the mixture is stirred at ambient temperature for 1 hour. After filtering, the layers are separated and the organic phase is washed with water. Triphenyl phosphine (26.2 g., 0.1 mole) is added to the benzene solution and it is heated to reflux. The precipitate which forms upon cooling is collected by filtration and dried to give β-formylvinylphosphonium chloride.

When an equivalent amount of β-formylvinylphosphonium chloride is allowed to react with formamidine sulfinic acid as described in the procedure of Example 4, (imidazolyl-4-methyl)triphenylphosphonium chloride is prepared.

Reaction of (imidazolyl-4-methyl)triphenylphosphonium chloride with cysteamine in the presence of sodium methoxide or sodium hydride as described hereinabove gives 4-(2-aminoethyl)thiomethylimidazole.

In a similar manner, the triphenylphosphonium group of (imidazolyl-4-methyl)triphenylphosphonium chloride is displaced by reaction with other nucleophiles by procedures described herein.

EXAMPLE 11

Tri-n-butylphosphine (20.2 g., 0.1 mole) is added to a solution of 10.4 g. (0.1 mole) of chlorovinyl methyl ketone in 250 ml. of benzene and the mixture is refluxed for 1 hour. The mixture is cooled and the precipitated material is collected by filtration and dried to give tri-n-butyl β-acetylvinylphosphonium chloride.

Triethyl β-acetylvinylphosphonium chloride is prepared as described above by use of triethylphosphine in place of tri-n-butylphosphine.

Reaction of an equivalent amount of tri-n-butyl β-acetylvinylphosphonium chloride or triethyl β-acetylvinylphosphonium chloride with formamidine sulfinic acid as described in the procedure of Example 4 gives [(5-methylimidazolyl)-4-methyl]tri-n-butylphosphonium chloride and [(5-methylimidazolyl)-4-methyl]-triethylphosphonium chloride, respectively.

Reaction of [(5-methylimidazolyl)-4-methyl]tri-n-butylphosphonium chloride or [(5-methylimidazolyl)-4-methyl]triethylphosphonium chloride with cysteamine in the presence of sodium methoxide or sodium hydride as described hereinabove gives 4-(2-aminoethyl)thiomethyl-5-methylimidazole.

EXAMPLE 12

Sodium amide (0.39 g., 0.01 mole) was dissolved in 40 ml. of liquid ammonia and 4.11 g. (0.01 mole) of [(5-methylimidazolyl)-4-methyl]triphenylphosphonium bromide was added. The suspension was stirred at −40° C. for 1 hour and then allowed to warm to room temperature as the ammonia evaporated. The triphenyl phosphine was extracted from the residue with benzene and the remaining solids were taken up in water and extracted with chloroform. The chloroform extracts were dried and evaporated to give 4-aminomethyl-5-methylimidazole in 70% yield. This amine was refluxed with a molar equivalent of cysteamine in acetic acid and treated with hydrochloric acid to give 4-(2-aminoethyl)thiomethyl-5-methylimidazole dihydrochloride.

EXAMPLE 13

[(5-Methyl-2-methylthioimidazolyl)-4-methyl]-triphenylphosphonium bromide (4.83 g., 0.01 mole) was stirred in 20 ml. of piperidine at room temperature for 30 minutes, then refluxed for 1 hour, cooled and filtered. The filtrate was evaporated under reduced pressure and chromatographed on a silica gel column using chloroform/methanol as eluant to yield 5-methyl-2-methylthio-4-piperidinomethylimidazole. Treating with hydrochloric acid and refluxing the resulting dihydrochloride salt with one molar equivalent of cysteamine in acetic acid gave 4-(2-aminoethyl)thiomethyl-5-methyl-2-methylthioimidazole dihydrochloride.

By the same procedure, using pyrrolidine in place of piperidine, 5-methyl-2-methylthio-4-pyrrolidinomethylimidazole is prepared.

Similarly, using morpholine in place of piperidine, 5-methyl-2-methylthio-4-morpholinomethylimidazole is prepared.

Converting these pyrrolidine and morpholine compounds to the dihydrochloride salts and treating with cysteamine in acetic acid gives 4-(2-aminoethyl)thiomethyl-5-methyl-2-methylthioimidazole dihydrochloride.

EXAMPLE 14

Dimethylamine (0.5 g., 0.01 mole) was dissolved in 35 ml. of tetrahydrofuran, stirred and cooled in an ice bath while 5 ml. (0.01 mole) of 2M butyl lithium in hexane was added dropwise with stirring. After stirring the mixture for 15 minutes in the cold, 3.93 g. (0.01 mole) of [(5-methylimidazolyl)-4-methyl]triphenylphosphonium chloride was added and the solution allowed to warm to room temperature. After stirring for 2 hours at room temperature, the solvents were evaporated and the residue treated with 50 ml. of water. Filtration yielded diphenyl phosphine. The aqueous filtrate was extracted with chloroform, dried and evaporated to afford 4-(N,N-dimethylaminomethyl)-5-methylimidazole. This amine was then refluxed with a molar equivalent of cysteamine in acetic acid and treated with hydrochloric acid to give 4-(2-aminoethyl)thiomethyl-5-methylimidazole dihydrochloride.

By the same procedure, using methylamine in place of dimethylamine, 4-(N-methylaminomethyl)-5-methylimidazole is prepared. In the same way, using butylamine and dibutylamine, 4-(N-butylaminomethyl)-5-methylimidazole and 4-(N,N-dibutylaminomethyl)-5-methylimidazole are prepared. Refluxing these intermediates with cysteamine by the above procedure and treating with hydrochloric acid gives 4-(2-aminoethyl)-thiomethyl-5-methylimidazole dihydrochloride.

EXAMPLE 15

N-Cyano-N'-methyl-N''-mercaptoethylguanidine (1.58 g., 0.01 mole) was dissolved in 15 ml. of methanol and 2.3 ml. of sodium methoxide in methanol was added. After stirring at room temperature for five minutes, a suspension of 3.93 g. of [(5-methylimidazolyl)-4-methyl]triphenylphosphonium chloride in 10 ml. of methanol was added. The solution was heated to reflux. An equal volume of water was added and most of the methanol was removed by evaporation. Filtration and water washing afforded triphenylphosphine. The filtrate was treated with charcoal, filtered and concentrated. Filtration gave N-cyano-N'-methyl-N''-[2-(5-methyl-4-imidazolylmethylthio)ethyl]guanidine.

EXAMPLE 16

A mixture of 6.6 g. (0.03 mole) of 4-(2-aminoethyl)thiomethyl-5-methyl-2-methylthioimidazole and 6.6. g. of 50:50 nickel-aluminum alloy in 50 ml. of formic acid was refluxed for 3 hours. The metals were removed by filtration and the filtrate was evaporated to dryness. The residue was dissolved in ethanol and the ethanolic solution was saturated with hydrogen sulfide then filtered. The filtrate was saturated with hydrogen chloride. Addition of ethyl acetate caused precipitation of 4-(2-aminoethyl)-thiomethyl-5-methylimidazole as the dihydrochloride salt.

In a similar manner, the 2-substituted thio group is removed from the other imidazole compounds in which $R^3$ is a substituted thio group prepared hereinabove.

Potassium carbonate (7.75 g.) was added to a solution of 14.6 g. of 4-(2-aminoethyl)thiomethyl-5-methylimidazole dihydrochloride in 120 ml. of water. The solution was maintained at ambient temperature for 15 minutes and 5.15 g. of methyl isothiocyanate was added. After heating under reflux for 0.5 hour, the solution was slowly cooled to 5°. The product was collected and recrystallized from water to give N-methyl-N'-[2-(5-methyl-4-imidazolylmethylthio)ethyl]thiourea, m.p. 150°–152°.

EXAMPLE 17

4-Methoxymethyl-5-methyl-2-methylthioimidazole (13.46 g., 0.078 mole) and ca. 25 g. of Raney nickel were added to 400 ml. of ethanol and the mixture was refluxed for 3 hours. The mixture was filtered and the filter cake was washed with 25 ml. of ethanol. The filtrate and washings were combined and hydrogen sulfide gas was passed into the solution for 10 minutes. The mixture was filtered and the filtrate was evaporated to dryness to give 8.63 g. (88%) of 4-methoxymethyl-5-methylimidazole.

4-Methoxymethyl-5-methylimidazole was converted to the corresponding hydrochloride salt as described above.

4-Methoxymethyl-5-methylimidazole hydrochloride (4.9 g., 0.03 mole) and 3.4 g. (0.03 mole) of cysteamine hydrochloride were dissolved in a minimum amount of acetic acid and the mixture was refluxed for 18 hours. After cooling in an ice bath, the mixture was filtered to give 5.8 g. (80%) of 4-(2-aminoethyl)thiomethyl-5-methylimidazole dihydrochloride salt.

Similarly, the other imidazoles prepared hereinabove in which $R^2$ is an alkoxy group and $R^3$ is a substituted thio group are reacted with Raney nickel followed by treatment of the product thus formed with cysteamine in acetic acid to give the corresponding 4-(2-aminoethyl)thiomethyl imidazoles.

(a) A solution of 17.0 g. of 4-(2-aminoethyl)-thiomethyl-5-methylimidazole and 11.2 g. of N-cyano-N',S-dimethylisothiourea in 500 ml. of acetonitrile was refluxed for 24 hours. The mixture was concentrated and the residue was chromatographed on a column of silica gel with acetonitrile as eluant. The product obtained was recrystallized from acetonitrile-ether to give N-cyano-N'-methyl-N''-[2-(5-methyl-4-imidazolylmethylthio)ethyl]-guanidine, m.p. 141°–142°.

(b) A solution of 23.4 g. of 4-(2-aminoethyl)-thiomethyl-5-methylimidazole in ethanol was added slowly to a solution of 20.0 g. of dimethyl-N-cyanoimidodithiocarbonate in ethanol, with stirring at ambient temperature. Filtration afforded N-cyano-N'-[2-(5-methyl-4-imidazolylmethylthio)ethyl]-S-methylisothiourea, m.p. 148°–150°. The filtrate was concentrated under reduced pressure and the mixture was triturated with cold water to give a solid material which was collected by filtration and recrystallized twice from isopropanol-ether, m.p. 148°–150°.

A solution of 75 ml. of 33% methylamine in ethanol was added to a solution of 10.1 g. of N-cyano-N'-[2-(5-methyl-4-imidazolylmethylthio)ethyl]-S-methylisothiourea in 30 ml. of ethanol. The reaction mixture was set aside at ambient temperature for 2.5 hours. Following concentration under reduced pressure, the residue was recrystallized twice from isopropanol-petroleum ether to give N-cyano-N'-methyl-N''-[2-(5-methyl-4-imidazolylmethylthio)ethyl]guanidine, m.p. 141°–143°.

EXAMPLE 18

Using [(2-methylthio-5-methylimidazolyl)-4-methyl]-triphenylphosphonium bromide in place of the phosphonium compound in the procedure of Example 15 gives N-cyano-N'-methyl-N''-[2-(2-methylthio-5-methyl-4-imidazolylmethylthio)ethyl]guanidine. The 2-methylthio group is removed by refluxing a mixture of the compound and 50:50 nickel-aluminum alloy in formic acid and working up by the procedure of Example 16 to give N-cyano-N'-methyl-N''-[2-(5-methyl-4-imidazolylmethylthio)ethyl]-guanidine.

What is claimed is:
1. A process for preparing a compound of the formula:

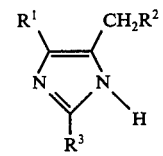

in which:
$R^1$ is hydrogen or lower alkyl;
$R^2$ is methoxy, ethoxy, n-propoxy, n-butoxy, i-butoxy, t-butoxy, —SCH$_2$CH$_2$NH$_2$ or

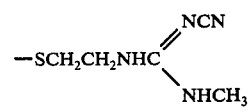

and $R^3$ is hydrogen, lower alkyl, trifluoromethyl, benzyl, amino or —SR$^4$ where $R^4$ is lower alkyl, phenyl, benzyl or chlorobenzyl, comprising reacting a compound of the formula:

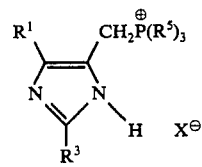

in which:
$R^1$ and $R^3$ are defined as above;
$R^5$ is a lower alkyl or phenyl; and
X is halo,
with a compound of the formula $R^2$—H where $R^2$ is defined as above in an organic solvent under basic conditions.

2. A process according to claim 1 in which $R^2$ is methoxy, ethoxy, n-propoxy, n-butoxy, i-butoxy, t-butoxy or —SCH$_2$CH$_2$NH$_2$.

3. A process according to claim 1 in which $R^5$ is phenyl.

4. A process according to claim 1 in which $R^2$ is —SCH$_2$CH$_2$NH$_2$ or

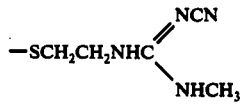

5. A process according to claim 4 in which $R^5$ is phenyl.

6. A process according to claim 3 in which $R^2$ is —SCH$_2$CH$_2$NH$_2$ and $R^3$ is —SR$^4$ where $R^4$ is methyl.

7. A process according to claim 3 in which $R^2$ is —SCH$_2$CH$_2$NH$_2$ and $R^3$ is hydrogen.

8. A process according to claim 3 in which $R^2$ is

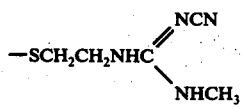

and $R^3$ is hydrogen.

9. A process according to claim 6 for preparing 4-(2-aminoethyl)thiomethyl-5-methyl-2-methylthioimidazole.

10. A process according to claim 7 for preparing 4-(2-aminoethyl(thiomethyl-5-methylimidazole.

11. A process according to claim 1 in which sodium methoxide or sodium hydride are used to provide the basic conditions.

12. A process according to claim 1 in which the solvent is methanol, ethanol, propanol, butanol, acetone, acetonitrile, dimethylformamide or dimethylsulfoxide.

13. A process according to claim 1 in which the reaction is carried out at a temperature of from about 25° C. to about 200° C. for from about 20 minutes to about 24 hours.

14. A process according to claim 13, in which the reaction is carried out at a temperature of about 65° C. to about 100° C. for from about 20 minutes to about 3 hours.

* * * * *